United States Patent [19]
Sato et al.

[11] Patent Number: 5,611,351
[45] Date of Patent: *Mar. 18, 1997

[54] METHOD AND APPARATUS FOR MEASURING BODY FAT

[75] Inventors: Tomio Sato, Tokyo; Hitoshi Sato, Tsurugashima; Koji Oguma, Fujisawa; Yoshinori Fukuda, Tokyo, all of Japan

[73] Assignee: Tanita Corporation, Tokyo, Japan

[*] Notice: The term of this patent shall not extend beyond the expiration date of Pat. No. 5,415,176.

[21] Appl. No.: 392,429

[22] Filed: Feb. 22, 1995

Related U.S. Application Data

[60] Division of Ser. No. 224,087, Apr. 6, 1994, Pat. No. 5,415,176, which is a continuation-in-part of Ser. No. 948,606, Sep. 23, 1992, abandoned.

[30] Foreign Application Priority Data

Nov. 29, 1991 [JP] Japan ................................. 3-339377

[51] Int. Cl.⁶ ............................................... A61B 5/05
[52] U.S. Cl. .................................................. 128/734
[58] Field of Search .......................... 128/734, 735, 128/774, 782, 779; 33/511, 512, 515; 177/4, 245; 364/413.01, 413.02

[56] References Cited

U.S. PATENT DOCUMENTS

| | | | |
|---|---|---|---|
| 3,192,627 | 7/1965 | Levitt et al. | 33/515 |
| 3,616,690 | 11/1971 | Harden | 177/245 |
| 3,667,561 | 6/1972 | Hutchinson et al. | 177/245 |
| 4,113,039 | 9/1978 | Ozaki | 177/25.19 |
| 4,336,855 | 6/1982 | Chen | 177/245 |
| 4,831,527 | 5/1989 | Clark | 364/413.02 |
| 4,870,341 | 9/1989 | Pihl et al. | 128/734 X |
| 4,883,066 | 11/1989 | Widdoes et al. | 128/774 |
| 4,895,163 | 1/1990 | Libke et al. | 128/734 |
| 4,911,175 | 3/1990 | Shizgal | 128/734 |
| 4,923,024 | 5/1990 | Ferrer et al. | 177/245 |
| 4,947,862 | 8/1990 | Kelly | 128/734 |
| 4,949,727 | 8/1990 | Yamazaki et al. | 128/734 |

FOREIGN PATENT DOCUMENTS 2215466  9/1989  United Kingdom.

OTHER PUBLICATIONS

Nakodomo et al. "Bioelectrical Impedance . . . Cross–Validity" Bioelectrical Impedance, vol. 41, pp. 467–476, 1992.
Segal et al. "Estimation of Human . . . A Comparative Study", The American Physiological Society, 1985, pp. 1565–1571.
Brozek et al. "Body Compsition" Annals of the New York Academy of Sciences, Sep. 26, 1963, vol. 110 pp. 113–140.

*Primary Examiner*—Guy V. Tucker
*Attorney, Agent, or Firm*—Keck, Mahin & Cate

[57] ABSTRACT

A body fat measuring apparatus for measuring body fat in a patient's body comprises apparatus for simultaneously measuring an impedance between the patient's feet, and for measuring the patient's height and the patient's weight, and a calculator for calculating body fat from the measured impedance value, height and weight. The calculator estimates body density using a formula having a correction term either for increasing the body density upon increase of the impedance compared to the original impedance or a correction term for decreasing the body density upon increase of the weight with respect to the original weight.

2 Claims, 3 Drawing Sheets

METHOD AND APPARATUS FOR MEASURING BODY FAT

CROSS REFERENCE TO RELATED APPLICATIONS

This application is a division of patent application Ser. No. 08/224,087, filed Apr. 6, 1994, now U.S. Pat. No. 5,415,176, which is a continuation-in-part of patent application Ser. No. 07/948,606, filed Sep. 23, 1992, now abandoned.

BACKGROUND TO THE INVENTION

1. Field of Invention

This invention relates to a method and apparatus for measuring body fat for measuring the amount of fatty tissue in vivo.

2. Description of the Prior Art

It has been customary to determine whether or not a human being is fat from the relationship between body weight and height.

However, it is not always unhealthy that weight is large in comparison with height, and it is important to measure fatty tissue in vivo. It is practical to measure body fat in vivo by measuring body weight. Recently, various body fat measuring instruments have been sold in the market.

An underwater body weighing method is known for estimating body fat by calculating body density from the measured weight value under water as a method for accurately measuring body fat in vivo.

This underwater body weighing method needs a large facility, and necessitates skillful measuring techniques and an effort by the person being measured considering the large influence of the amount of residual air in the lungs to be measured.

In order to eliminate the disadvantages of the above-described underwater body weighing method, there has been proposed a method for estimating body density by measuring body impedance between extremities of the body and estimating the body density from the measured impedance value, height and body weight.

The ratio of body water in fat-free tissue of body composition tissue is constant and the specific resistance of the fat-free tissue is constant. The estimation formula: body density=$1.1554-0.0841*weight*impedance/(height)^2$ of Segal et al., and body formula: density=$1.1303-0.726*weight*impedance/(height)^2$ of Naka et al., by obtaining the inference formula as represented by body density=$A-k*weight*impedance/(height)^2$, and obtaining correlation between the constant A and the value obtained actually by an underwater body weighing method for determining the constants A and k, are disclosed.

However, it is known that the impedance value varies due to various factors such as variation in body water ratio in fat-free tissue due to variation in body weight, amount of blood plasma due to variation in motion or attitude and movement of interstitial liquid. In order to accurately measure the impedance value, it is necessary to consider influences of ingestion of food and water, motion, attitude and variation in body weight.

Thus, the impedance value of a body to be measured vary according to the date, time and differences of body condition before measurement. These various are too large to use the above-described inference formula accurately and amount of body fat calculated by the formula is likely to be inaccurate.

Therefore, in order to measure accurately, it is necessary to maintain the body state of the patient to be measured constant by selecting a day for taking the measurements when ingestion of food and water, and activity, are limited and variation in body weight is small, and to measure the impedance value after the patient has been lying on a bed for a predetermined period of time. Thus, the measuring conditions are known.

On the other hand, there has also been proposed a method for calculating body fat from numeric values with respect to a body such as an impedance between extremities of the body, height, weight and gender by measuring the impedance using a 4-terminal Kelvin bridge living body impedance meter as a method for accurately and simply measuring the body fat in vivo as in U.S. Pat. Nos. 4,008,712 and 4,895,163 (Japanese Patent Laid-open No. Hei 2-60626).

Since the degrees of bending and the angle of the limbs influence the impedance values using these methods, the measuring conditions when the patient is lying on a bed are maintained constant to eliminate errors.

Further, if the spacing between a current supply terminal and a voltage detecting terminal of electrodes for detecting the impedance is not sufficient, the measured values are affected, and hence the spacing is maintained by mounting the current supply terminals on the backs of the hand and foot and mounting the voltage detecting terminals on the tendons of the wrist and the ankle.

Accordingly, restrictions in the measuring position are significant (needs a bed, etc.), and it is difficult for a person to use the apparatus to take measurements of himself without assistance.

Moreover, in a method for measuring living body impedance, it has also been necessary to measure body fat as described above, using a method having steps of outputting a sine wave of 50 kHz from an oscillator as a constant-voltage source, converting it to a constant current of 800 microamperes by a voltage/current converter, supplying the current through a pair of electrodes mounted on a body, outputting the voltage value of a voltage drop from a pair of electrodes mounted inside the above-described electrodes by a differential amplifier, waveform-shaping, rectifying it, DC-converting it, then, A/D-converting it as digital data, and applying it to a calculator, determining the living body impedance Z by $Z=V/I$ from the living body current I and the terminal voltage V, and measuring the voltage V when the current I is Constant, thereby determining the living body impedance Z.

However, the constant-current source is affected and its output is varied due to the influence of the external environmental temperature, etc., by the degree of variation in the electrode impedance, and it is difficult to obtain an accurate value of the living body current I as an accurate constant current, thereby causing error in measuring the living body impedance.

On the other hand, the living body impedance to be measured by a body fat meter needs to be accurate in a wide range of 0 to about 1 kilo-ohm. It is extremely difficult to obtain an ideal proportional relation in this range, thereby necessitating a great deal of work for making corrections to the measured value.

Accordingly, an object of this invention is to provide a method and apparatus for measuring body fat which has a small restriction in measuring conditions and which can be simply measured without influence by the measuring conditions.

Another object of this invention is to provide a practical body fat measuring apparatus which can be readily used by the person being measured without restriction.

Still another object of this invention is to provide a living body impedance measuring method which is particularly adapted for measuring body fat and can accurately measure the absolute value of the living body impedance in a wide measuring range without influence of the environment.

SUMMARY OF THE INVENTION

According to an aspect of this invention, there is provided a method for measuring body fat by the steps of measuring impedance between extremities of a body, estimating body density from the measured impedance value, measuring the height and the weight, and calculating the body fat, comprising the step of estimating a body density by a calculation formula having one of a correction term for increasing the body density upon increase of the impedance with respect to only the impedance and a correction term for decreasing the body density Upon increase of the weight with respect to only the weight.

According to another aspect of this invention, there is provided a body fat measuring apparatus for measuring body fat in a patient's body comprising a measuring station for simultaneously measuring an impedance between extremities of the patient's body, a patient's height and a patient's weight, and a calculator for calculating body fat from the measured impedance value, height and weight, whereby the body density is estimated by a calculation formula having one of a correction term for increasing the body density upon increase of the impedance with respect to only the impedance and a correction term for decreasing the body density upon increase of the weight with respect to only the weight.

According to still another aspect of this invention, there is provided a body fat measuring apparatus having the steps of measuring an impedance between extremities of a body, and calculating body fat from numeric values of physical conditions such as the measured body impedance value, height, weight, and gender comprising a pair of conductive electrodes for contacting the patient's toes defined as current supply terminals at a nearest interval of 5 cm or more, and a pair of electrodes for contacting a patient's heels defined as voltage detecting terminals on an insulating base having protrusions for heel guides in such a manner that, when the patient stands thereon, the electrodes are mounted to protrude from the base symmetrically with respect to the width of the base spaced apart for the patient to stand in an upright position so that the patient's feet are not touching and the patient's body impedance can be measured in the standing position.

According to still another aspect of this invention, a method for measuring impedance of a person is provided which comprises the steps of inserting a plurality of reference resistors in a current path for supplying a current to a living body, measuring voltage drops of the reference resistors by momentarily switching the reference resistor group and the living body to obtain a correlation formula between the measured value by the reference resistors and the impedance, and determining the impedance of the living body by the patient's measured value and the correlation formula.

This invention will now be described in further detail with respect to preferred embodiments as illustrated in the accompanying drawings.

DESCRIPTION OF THE PREFERRED EMBODIMENTS

Figure 1:
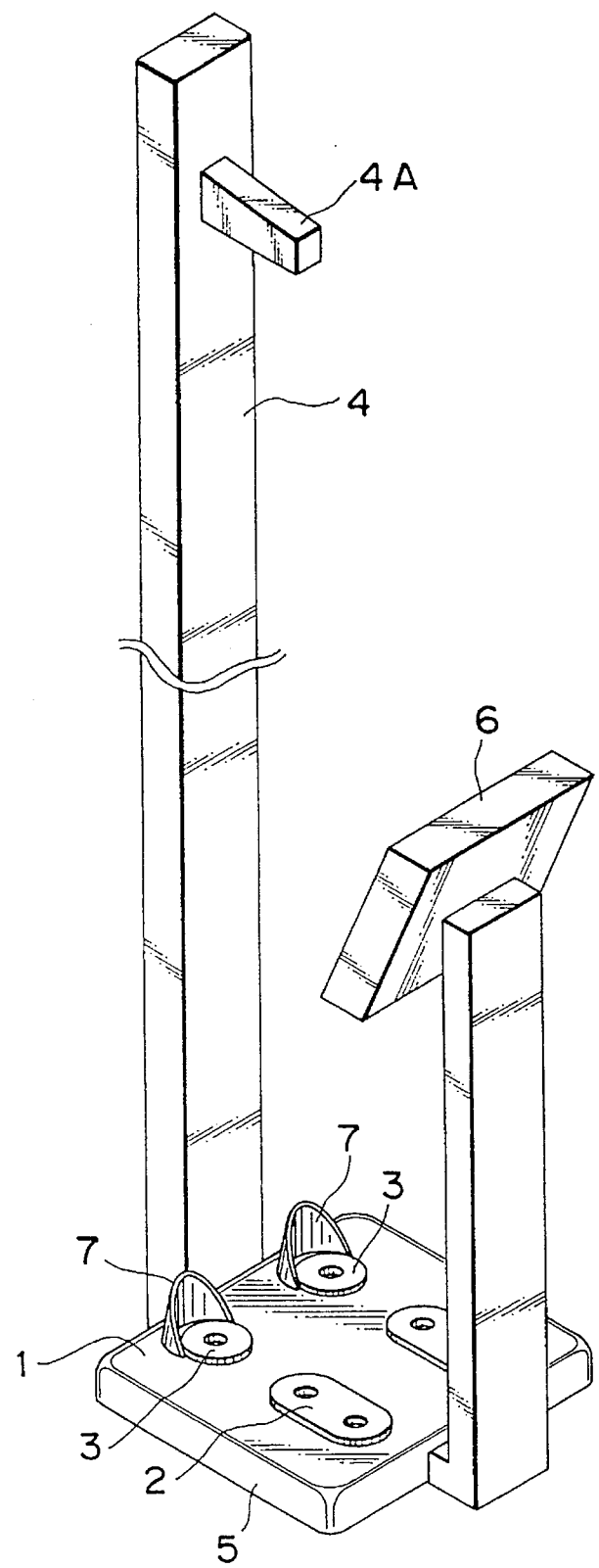
FIG. 1 is a schematic perspective view of a body fat measuring apparatus showing an embodiment of the present invention.

Referring to FIG. 1, a body fat measuring apparatus is shown as an embodiment of the present invention. This apparatus comprises an electronic body weighing meter 5 having a base 1 on its upper surface, an electronic height meter 4, and a display unit 6. This electronic body weighing meter 5 electronically calculates a patient's body weight when a patient stands on the base 1. The electronic height meter 4 detects the height of a patient standing on the base 1 using a detector 4A and electronically calculates the height value.

Figure 2:
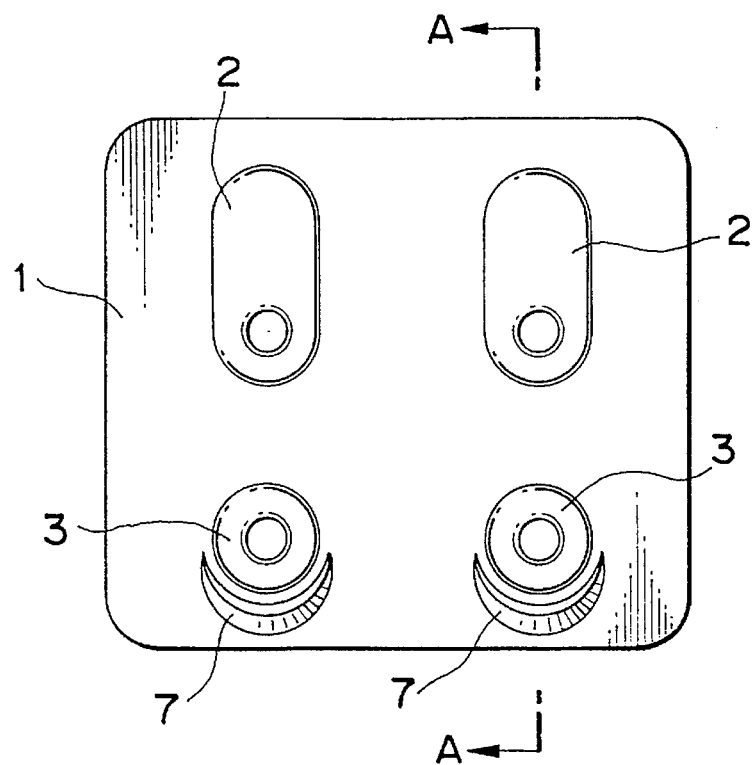
FIG. 2 is a plan view showing, in detail, a base of a body weighing apparatus of FIG. 1.
Figure 3:
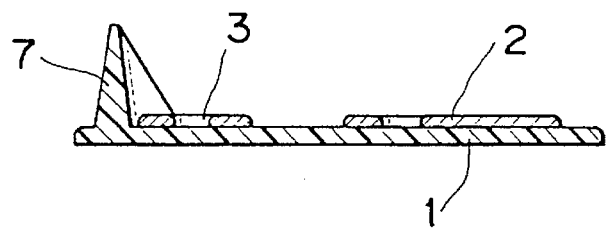
FIG. 3 is a sectional view taken along the line 3—3 of FIG. 2.

As shown in FIGS. 2 and 3, the base 1 is formed of an insulating material, and a pair of conductive electrodes 3 for a patient's heels and conductive electrodes 2 for a patient's toes are mounted symmetrically with respect to the width of the base spaced to allow the patient to stand upright so that the patient's feet are not touching when the patient stands thereon on both feet. The electrodes 2 and 3 are set to 5 cm or more apart so as to eliminate the influence of a potential distribution. The electrodes 2 are formed in an elliptical shape so as to correspond to various sizes of a patient's foot. The electrodes 2 are used as current supply electrodes, and the electrodes 3 are used as voltage detecting terminals.

Heel guides 7 are provided at the rear of the electrodes 3 so that a user can always stand at a predetermined position on the base 1 with his heels in contact with the electrodes.

Figure 4:
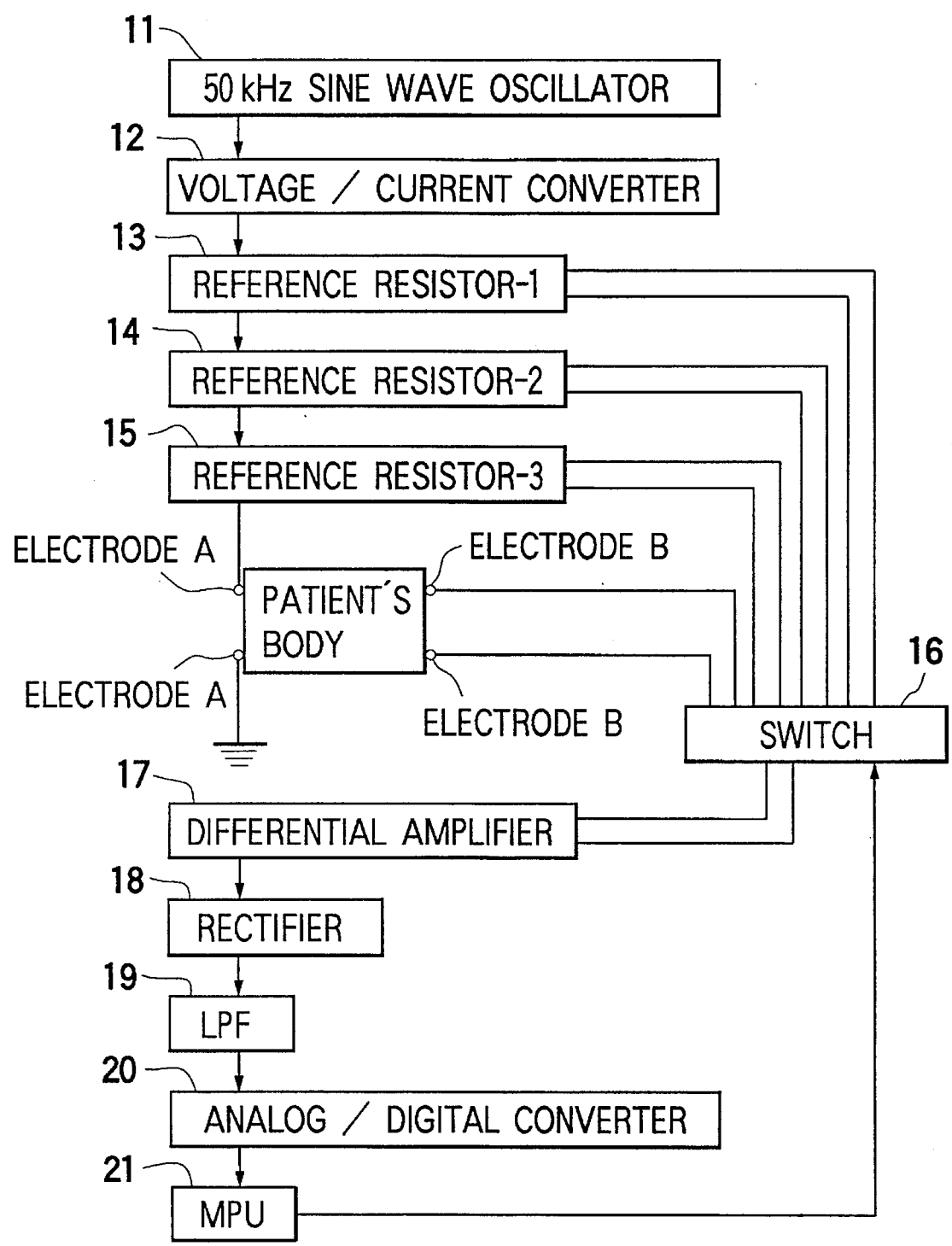
FIG. 4 is a block diagram showing an example of a circuit arrangement for carrying out a living body impedance measuring method according to the present invention.

An electronic circuit for carrying out a body impedance measuring method according to the present invention is placed in the housing of the electronic body weighing meter 5, and an example of the electronic circuit is shown in a block diagram of FIG. 4. In FIG. 4, electrodes A correspond to the electrodes 2 for the patient's toes in FIGS. 1 to 3, and electrodes B correspond to the electrodes 3 for the patient's heels in FIGS. 1 to 3.

The body impedance measuring electronic circuit in FIG. 4 measures a patient's body impedance when a patient stands on the base 1 of the apparatus in FIG. 1 in such a manner that the patient's toes and heels are contacted correspondingly with the electrodes 2(A) and the electrodes 3(B).

An oscillator 11 generates a sine wave of 50 kHz as a constant-voltage source, which is converted to a constant current of 800 microamperes by a voltage/current converter 12, which does not affect influence to linearity of a body impedance. The constant current is supplied from a pair of electrodes A through a plurality of reference resistors 12, 14, 15 having known resistances to cover an average measuring range (a range necessary to measure an impedance between the extremities of a patient's body as individual differences: 0 to 1 kilo-ohm).

Values of voltage drops of the reference resistors 13, 14, 15 in a group, and values of voltage drops of the pair of electrodes B mounted inside a living body from the electrodes A are momentarily switched by a switch 16 to be controlled by a microprocessor unit (MPU) 21 which includes a calculator, and differences therebetween are output by a differential amplifier 17. The voltage value output by the differential amplifier 17 is rectified by a rectifier 18, waveform-shaped by a low pass filter (LPF) 19 to be DC-converted, A/D-converted by an analog/digital converter (AD) 20, and input as digital data to the microprocessor unit 21 obtains a correlation formula between the measured value of the reference resistor and the impedance, and determines a living body impedance from the measured value of the patient's living body and the correlation formula.

An electronic circuit for using in a body fat measuring method according to the present invention is also associated in the housing of the electronic body weighing meter 5. This body fat measuring electronic circuit calculates a patient's body fat as below from the patient's weight measured by the electronic body weighing meter 5, the patient's height measured by the electronic height meter 4 and the patient's body impedance calculated by the above-described body impedance measuring electronic circuit.

An inference formula of body density (DB) of Segal et al., using weight (W), height (Ht) and impedance (Z), is represented by:

$$DB = A - k*W*Z/Ht^2 \quad (1)$$

where

A is a constant, k is a proportional coefficient

The value proportional to the weight and the impedance Z and inversely proportional to the square of the height is subtracted from the constant A.

However, as described above, it is known that the impedance value varies due to various factors such as variation in body water ratio in fat-free tissue due to variation in weight, blood plasma due to variation in motion or attitude and movement of interstitial liquid in a short period. The variation in the impedances greatly influences the body density in the formula (1), but the variation factor of the impedance does not originally greatly vary the body density.

In order to reduce the influence of the variation in the impedances to the body density, a correction term for reversely affecting the influence of the variation in the impedances of the formula (1) to the body density, i.e., a correction term for increasing the body density if the impedance is increased is provided as a third term, and a corrected reference formula is represented by:

$$DB = A - k'*W*Z/Ht^2 + k''*Z \quad (2)$$

where k' and k'' are proportional coefficients.

On the other hand, the above-described assumption is based on the premise that the variation in the weight is small with respect to the variation in the impedance, and it can be corrected if the variation in weight is responsive to the variation on the measured impedance. It is replaced by providing the correction term for performing the same operation as the influence of the variation in the weight in the formula (1) to the body density, i.e., the correction term for reducing the body density if the weight is increased as a third term, and a correction formula is represented by:

$$DB = A - k'*W*Z/HT2 - k''*W \quad (3)$$

In order to reduce measuring conditions of an impedance between a patient's feet, with the patient in a standing attitude, and to accurately measure the impedance, tests were conducted by a number of subjects under various conditions to obtain correlation between the above-described assumption and an underwater body weighing method, and most desirable coefficients in the formulae (2) and (3) have been decided.

The coefficients A, k' k'' may be determined experimentally and/or statistically so that the equations provide measures of body density which most closely approximate those measured by means of an underwater body weighing method.

The following formula could be obtained as a most suitable inference formula for estimating a patient's body density by using the impedance value between both of the patient's feet in a standing position based on the formula (2):

$$\text{Body density} = 1.1144 - 0.0976*W*Z/Ht^2 + 0.000084*Z$$

where

W: body weight (kg)

Z: impedance (ohm)

Ht: height (cm)

On the other hand, the following formula could be obtained as a most suitable inference formula for estimating a patient's body density by using the impedance value between both of the patient's feet in a standing position based on the formula (3):

$$\text{Body density} = 1.1442 - 0.0626*W*Z/Ht^2 - 0.00044*W$$

where

W: body weight (kg)

Z: impedance (ohm)

Ht: height (cm)

Body fat can be obtained by the following formula:

$$\text{body fat } (\%) = (4.57/\text{body density} - 4.142)*100$$

The correlation to the underwater body weighing method of the result for calculating the body fat by the above-described inference formula is of the same degree as that for fixing the measuring conditions without a correction term, the variation due to the difference of the measuring conditions is reduced to ½ of that without the correction term, thereby obtaining a satisfactory result.

According to the present invention, body fat can be concurrently measured in a standing position with extremely small error in the measurements by correcting the inaccuracy of the measured values due to the variation in the impedance value according to the measuring conditions.

Further, the body fat measuring apparatus according to the present invention can readily be used by a user to measure his body fat by himself merely by standing upright at a designated position, and he can repeatedly measure it under the same conditions and can also take the measurements in the standing position. Therefore, restrictions in the mounting position of the measuring instrument are remarkably reduced.

We claim:

1. A method of measuring impedance of a patient's body comprising the steps of:

connecting a plurality of reference resistors each having a known resistance in series with said patient's body;

supplying an electric current into a current path through said plurality of reference resistors and said patient's body;

measuring voltage drops across any of said reference resistors and/or measuring voltage drops across any groups of adjacent said reference resistors, and measuring a voltage drop due to said patient's body by momentarily and successively switching over a voltage drop measuring device for each of said voltage drops;

obtaining a correlation formula between said known resistances of said reference resistors and impedance of said patient's body, based on measured values of said voltage drops; and determining the impedance of said patient's body by using the measured value of the voltage drop due to said patient's body and said obtained correlation formula.

2. An apparatus for measuring impedance of a patient's body comprising a pair of input electrodes and a pair of output electrodes adapted to contact with spaced-apart portions of said patient's body;

a plurality of reference resistors each having a known resistance connected in series with said input electrodes;

means for supplying an electric current into a current path through said plurality of reference resistors, said input electrodes and said portions of the patient's body;

voltage drop measuring means;

switching means for momentarily and successively switching over said voltage drop measuring means across any of said reference resistors and/or across any groups of adjacent said reference resistors, and across said pair of output electrodes to measure voltage drops across the said reference resistors and/or voltage drops across the groups of said reference resistors, and a voltage drop due to said patient's body when said current supplying means supplies an electric current into said current path; and processing means for obtaining a correlation formula between said resistances of said reference resistors and impedance of patient's body on the basis of values of said voltage drops measured by said voltage drop measuring means and determining the impedance of said patient's body by using the measured value of the voltage drop due to said patient's body and said obtained correlation formula.

* * * * *